United States Patent
Bohlen

(10) Patent No.: US 9,606,044 B1
(45) Date of Patent: Mar. 28, 2017

(54) DEPRESSURIZATION TEST METHOD USING PRESSURE VESSEL

(71) Applicant: Space Systems/Loral, LLC, Palo Alto, CA (US)

(72) Inventor: Terry Bohlen, Campbell, CA (US)

(73) Assignee: Space Systems/Loral, LLC, Palo Alto, CA (US)

( * ) Notice: Subject to any disclaimer, the term of this patent is extended or adjusted under 35 U.S.C. 154(b) by 442 days.

(21) Appl. No.: 14/222,136

(22) Filed: Mar. 21, 2014

(51) Int. Cl.
*G01N 19/08* (2006.01)

(52) U.S. Cl.
CPC .................. *G01N 19/08* (2013.01)

(58) Field of Classification Search
CPC ..... B64F 5/0045; G01M 3/26; G01M 5/0016; G01M 3/04; G01M 3/3209; A62B 17/008; B64D 10/00; B64D 2010/002; B64D 2010/005; G01P 21/00; G01N 19/08
See application file for complete search history.

(56) References Cited

U.S. PATENT DOCUMENTS

| 3,399,574 | A | * | 9/1968 | Seiler | G01M 3/3209 |
| | | | | | 73/49.2 |
| 3,593,567 | A | * | 7/1971 | Hartley | G01P 21/00 |
| | | | | | 73/40 |
| 5,318,018 | A | * | 6/1994 | Puma | A62B 17/008 |
| | | | | | 128/202.11 |
| 5,755,234 | A | * | 5/1998 | Mobley | A61F 11/08 |
| | | | | | 128/864 |
| 6,439,048 | B1 | * | 8/2002 | Hui | G01P 13/025 |
| | | | | | 73/181 |
| 7,204,125 | B2 | | 4/2007 | Fine et al. | |
| 2013/0000247 | A1 | | 1/2013 | Sypeck | |
| 2014/0162542 | A1 | * | 6/2014 | Huart | B64D 13/02 |
| | | | | | 454/74 |

* cited by examiner

*Primary Examiner* — Daniel S Larkin
*Assistant Examiner* — Jamar Ray
(74) *Attorney, Agent, or Firm* — Weaver Austin Villeneuve & Sampson LLP

(57) ABSTRACT

Techniques for testing a component for compatibility with a depressurization profile associated with a launch vehicle payload fairing during ascent are disclosed. A pressure of air or other gas within a pressure vessel containing the component is raised to a first value substantially higher than one atmosphere absolute pressure. The air/gas pressure within the pressure vessel is lowered, by venting into the ambient atmosphere, at a rate simulating or demonstrating margin with respect to the launch vehicle payload fairing depressurization profile. The component is inspected for damage. The component may be a panel including a honeycomb core sandwiched between two faceskins, the panel having a planar area in excess of twenty five square feet.

19 Claims, 4 Drawing Sheets

*Exploded isometric view*

*View A-A*

*View B-B*

DEPRESSURIZATION TEST METHOD USING PRESSURE VESSEL

TECHNICAL FIELD

This invention relates generally to spacecraft structural testing, and, more particularly, to testing the venting capacity of large structures.

BACKGROUND OF THE INVENTION

The assignee of the present invention manufactures and deploys spacecraft for, inter alia, communications and broadcast services from geostationary orbit. During launch, such spacecraft are enclosed within a launch vehicle payload fairing that experiences depressurization to a near vacuum condition from an initial pressure of nominally one atmosphere (approximately 14.7 PSIA) within a time period of about two minutes. To safely accommodate this pressure change, the spacecraft design must include provisions for safely venting of air from interior volumes of the spacecraft and spacecraft components into the launch vehicle payload fairing.

Large structural components of a spacecraft include spacecraft equipment and solar array panels and structural panels that may be in the range of 60 to 80 square feet surface area. Referring to FIG. 1, an exploded isometric view of a typical panel 100 is illustrated. Panel 100 includes a honeycomb core 110 sandwiched between panel faceskins 120. The panel face skins 120 may be adhered to a honeycomb core 110 by epoxy adhesive or other adhesive bond, for example. Referring now to views A-A and B-B of FIG. 1 each cell in the honeycomb core is intended to be vented (by slitting or perforating, for example) to permitted air to escape during launch as the spacecraft leaves the earth's surface and experiences a depressurization from approximately one atmosphere of pressure to the vacuum of space.

In practice, however, it has been found that some cells of an as-fabricated honeycomb panel may exhibit manufacturing defects as a result of which the defective cells fail to comply with the design intent of providing safe venting means. Such manufacturing flaws are difficult to completely prevent and may be difficult to detect by conventional inspection or nondestructive test techniques. A consequence of such undetected flaws can include explosive rupture of the panel, and resulting damage to spacecraft functional systems.

As a result, an improved approach to testing the venting capacity of such structures is desirable.

SUMMARY

The present disclosure contemplates improved techniques for testing a spacecraft component for compatibility with a depressurization profile associated with a launch vehicle ascent.

In an implementation, a component is tested for compatibility with a depressurization profile associated with a launch vehicle ascent. The testing includes raising a pressure within a pressure vessel containing the component to a first value substantially higher than one atmosphere absolute pressure, lowering the pressure within the pressure vessel at a rate simulating the depressurization profile, and inspecting the component for damage.

In some implementations, the first value may be at least two atmospheres absolute pressure.

In some implementations, the component may be a panel comprising a honeycomb core sandwiched between two faceskins. A planar area of the panel may be at least 25 square feet.

In some implementations, the rate simulating the depressurization profile averages approximately 0.5 atmospheres per minute. Lowering the pressure of the pressure vessel at the rate of approximately 0.5 atmospheres per minute may be performed for a duration of greater than one minute. Lowering the pressure of the pressure vessel at the rate of approximately 0.5 atmospheres per minute may be performed by venting the test chamber to a pressure no less than ambient pressure.

In some implementations, the rate simulating the depressurization profile may have a maximal value of at least one atmosphere per minute.

In some implementations, raising the pressure may result in achieving substantially equal pressures in the pressure vessel exterior to the component and in interior portions of the component.

In some implementations, the pressure vessel may be an autoclave.

In an implementation, a method includes testing a component for compatibility with a depressurization profile associated with a launch vehicle ascent. The testing includes raising a pressure within a pressure vessel containing the component to a first value substantially higher than one atmosphere absolute pressure, lowering the pressure within the pressure vessel at a rate demonstrating margin with respect to the depressurization profile, and inspecting the component for damage.

BRIEF DESCRIPTION OF THE DRAWINGS

Features of the invention are more fully disclosed in the following detailed description of the preferred embodiments, reference being had to the accompanying drawings, in which.

Figure 1:
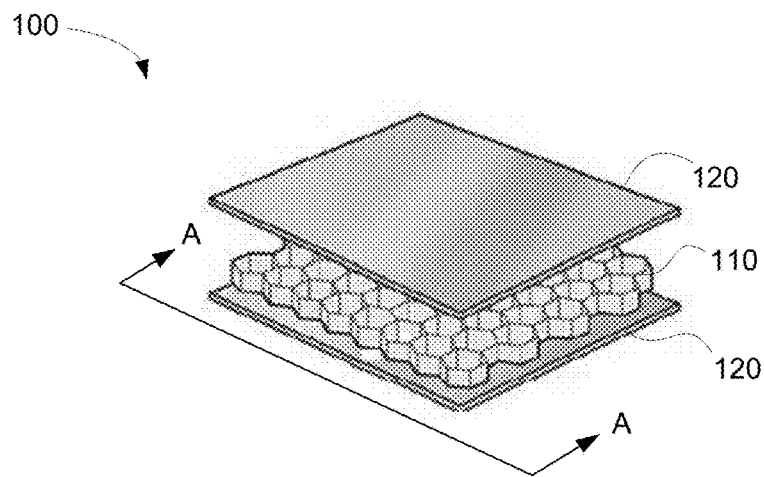
FIG. 1 illustrates an example of a spacecraft structural component to which implementations of the invention may be applied.
Figure 1:
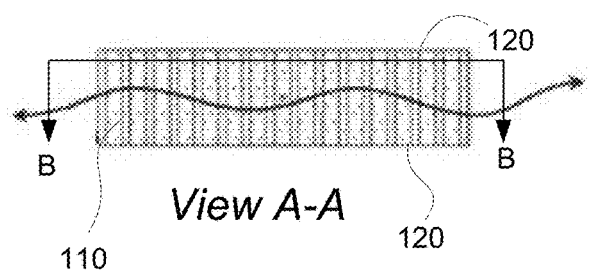
Figure 1:
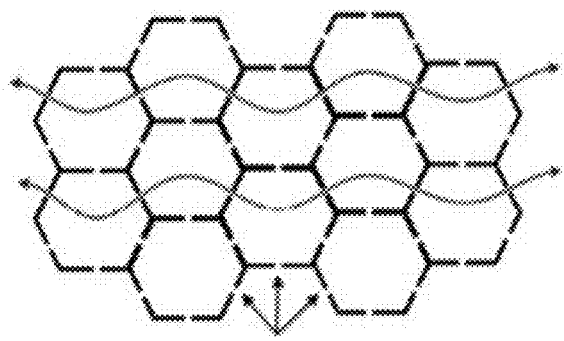

Throughout the drawings, the same reference numerals and characters, unless otherwise stated, are used to denote like features, elements, components, or portions of the illustrated embodiments. Moreover, while the subject invention will now be described in detail with reference to the drawings, the description is done in connection with the illustrative embodiments. It is intended that changes and modifications can be made to the described embodiments without departing from the true scope and spirit of the subject invention as defined by the appended claims.

DETAILED DESCRIPTION

Specific examples of embodiments will now be described with reference to the accompanying drawings. This invention may, however, be embodied in many different forms, and should not be construed as limited to the embodiments set forth herein. Rather, these embodiments are provided so that this disclosure will be thorough and complete, and will fully convey the scope of the invention to those skilled in the art.

It will be understood that when an element is referred to as being "connected" or "coupled" to another element, it can be directly connected or coupled to the other element, or intervening elements may be present. It will be understood that although the terms "first" and "second" are used herein to describe various elements, these elements should not be limited by these terms. These terms are used only to distinguish one element from another element. As used herein, the term "and/or" includes any and all combinations of one or more of the associated listed items. The symbol "/" is also used as a shorthand notation for "and/or".

Figure 2:
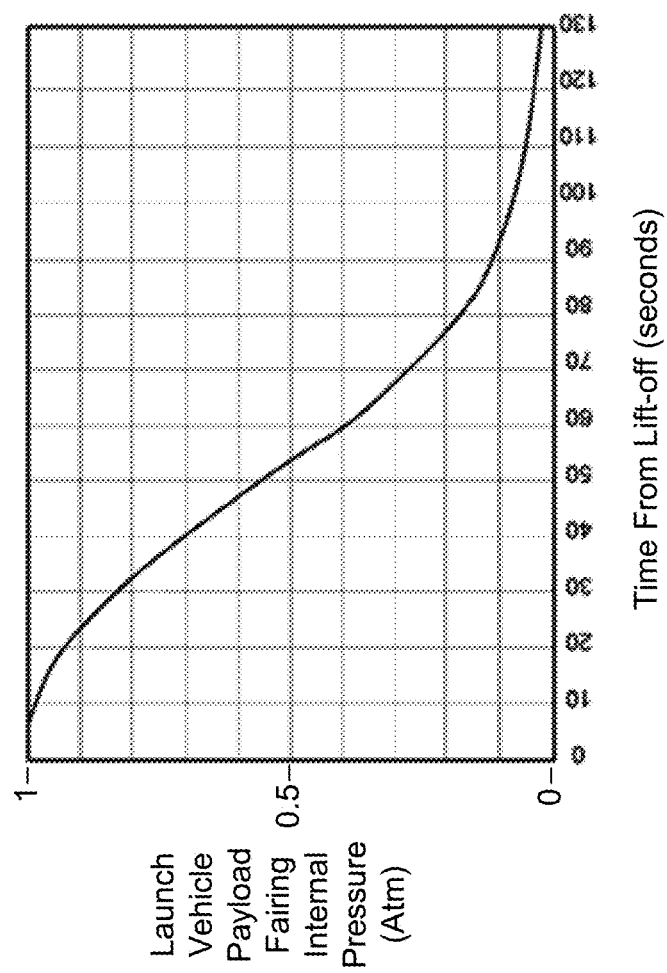
FIG. 2 illustrates an example of a pressure profile within a launch vehicle payload fairing during launch vehicle ascent.

The presently disclosed techniques permit validation by ground test that a test article such as a spacecraft component is able to withstand decompression at the rapid rates associated with launch vehicle ascent. Referring now to FIG. 2, an example of a pressure profile within a launch vehicle payload fairing during launch vehicle ascent is illustrated. In the illustrated example, pressure within the payload fairing decreases from one atmosphere to approximately a vacuum in approximately 130 seconds. It may also be observed that a depressurization rate may vary during launch vehicle ascent, and may reach a peak depressurization rate in excess of one atmosphere per minute.

According to the presently disclosed techniques, compatibility of a test article with a pressure profile such as the one illustrated in FIG. 2 may be demonstrated by over pressurizing, with respect to ambient pressure, a pressure vessel in which the test article is installed and then rapidly depressurizing the pressure vessel to or near to ambient pressure. Since the pressure difference and rate of change of the pressure difference between the exterior and interior spaces of the test article during the launch vehicle ascent and the structural capability of the test article to safely withstand the pressure difference without damage is of interest, the test technique test focuses on the pressure difference and the pressure difference rate of change, not the absolute starting and ending pressures during the launch vehicle ascent.

Figure 3:
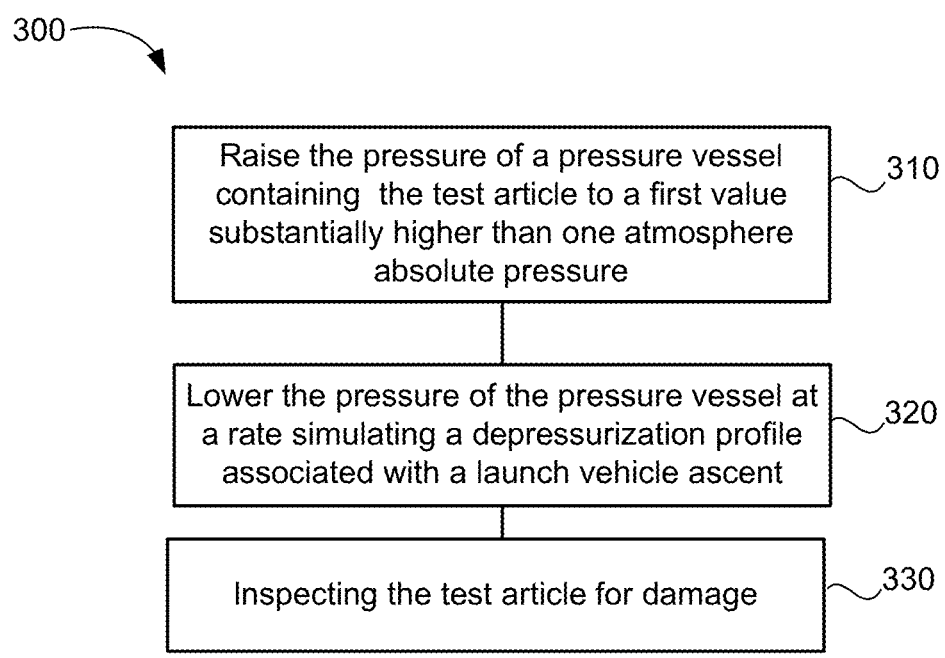
FIG. 3 illustrates an example implementation of the disclosed test techniques.

Referring now to FIG. 3, an example of a method for determining whether a test article is able to withstand the pressure profile will be described. The method 300 may include a step 310 of raising the pressure of air (or other gas) within a pressure vessel containing the test article to a first value substantially higher than one atmosphere absolute pressure. The first value may be approximately 2 atmospheres absolute pressure or higher, for example.

In some implementations, raising the pressure results in achieving substantially equal pressures in the pressure vessel exterior to the test article and in interior portions of the test article. For example, the pressure vessel may be held at an elevated pressure for a period of time sufficient to thoroughly "soak" interior portions of the test article at the elevated pressure within the pressure vessel. As a result, it may be ensured that internal spaces within the test article will be at the same pressure as the pressure within the pressure vessel.

In some implementations, the pressure vessel may be an autoclave. The pressure vessel may be of a size sufficient to accommodate a large structural component such as a spacecraft equipment panel or solar array panel. In some implementations the pressure vessel may be approximately 10 feet in diameter, for example. In some implementations, the pressure vessel may have an internal volume of at least 1000 cubic feet.

At step 320, the pressure within the pressure vessel may be lowered at a rate simulating a depressurization profile associated with a launch vehicle ascent. In some implementations, lowering the pressure may be accomplished by opening a pressure vessel gate valve or similar apparatus. As a result of opening the pressure vessel gate valve, air or other pressurized gas within the pressure vessel may be allowed to escape to an ambient environment. A rate at which the pressurized gas exits the pressure vessel may be controlled by, for example, judicious operation of the pressure vessel gate valve. Correspondingly, a depressurization rate of the pressure vessel may be controlled so as to simulate or exceed the depressurization profile associated with the launch vehicle ascent.

It will be appreciated that the depressurization rate may also be controlled so as to demonstrate margin with respect to the depressurization profile. For example, if the maximum expected depressurization rate during the launch vehicle ascent is one atmosphere per minute, the depressurization rate of the pressure vessel may be controlled to provide a maximum depressurization rate of 1.5 atmospheres per minute.

At step 330, the test article may be inspected for damage. Inspecting the test article may include, for example, a visual inspection of the face skins of a honeycomb panel to determine whether the test sequence resulted in deformation or rupture of the face skins. The face skins may also undergo other nondestructive testing techniques, such as a flatness test, for example.

Figure 4:
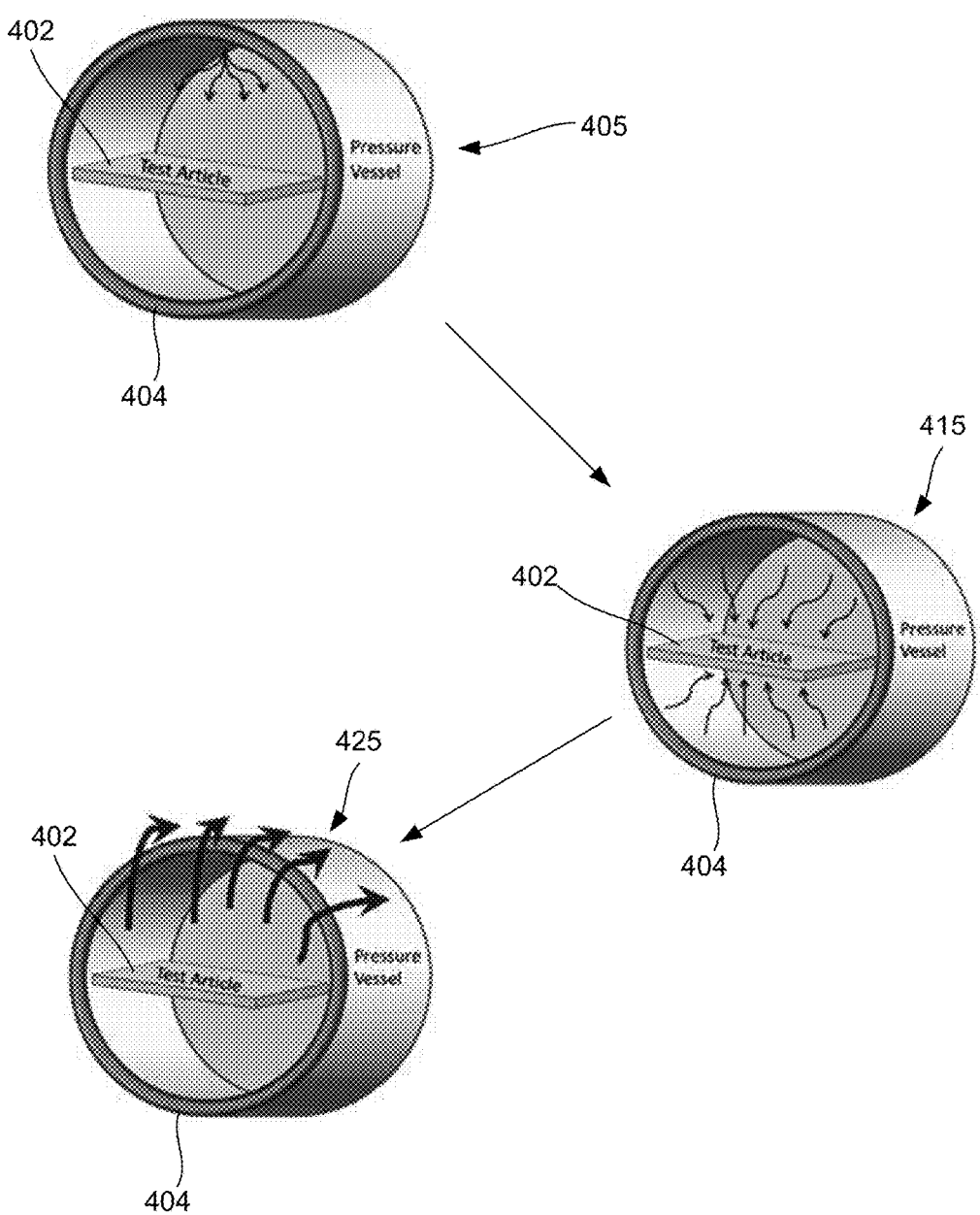
FIG. 4 illustrates another example implementation of the disclosed test techniques.

A better understanding of features and benefits of the presently disclosed techniques may be obtained by referring now to FIG. 4. In a first mode 405, a test article 402 is disposed within a pressure vessel 404. The test article 402 may be a large structural component of a spacecraft. For example, the test article 402 may be an equipment panel or a solar array panel of the spacecraft. In some implementations, the test article 402 may include a honeycomb core sandwiched between two faceskins. A planar area of the test article 402 may be in the range of 25 to 100 square feet, or greater, for example.

In some implementations, the pressure vessel 404 may be an autoclave. During the first mode 405, the pressure vessel 404 may be over pressurized with respect to ambient external air pressure. In some implementations, pressure within the pressure vessel 404 may be slowly increased to an elevated pressure. For example, the elevated pressure may be raised to two atmospheres absolute pressure or greater over a period of several minutes.

In a second mode 415, the test article 402 may be soaked at the elevated pressure for a period of time. The period of time may be selected so that internal volumes of the test article 402 reach a steady state pressure equal to the elevated pressure within the pressure vessel 404. The period of time may be, for example, one hour.

In a third mode 425, the pressure vessel 404 may be rapidly depressurized. In some implementations, for example, a gate valve or similar apparatus of the pressure vessel 404 may be opened such that air, or other pressurized gas within the pressure vessel 404 rapidly escapes to the ambient environment. As a result, the test article 402 may be caused to experience a depressurization profile, when pressure within the pressure vessel 404 is vented to ambient pressure. The depressurization profile may be similar to or in excess of that experienced during launch ascent. In some implementations, the depressurization profile may average approximately 0.5 atmospheres per minute. In some implementations the depressurization profile may include a peak depressurization rate of one atmosphere per minute or greater, for example. In some implementations, the depressurization profile may include lowering the pressure of the pressure vessel 404 at the rate of approximately 0.5 atmospheres per minute for a duration of greater than one minute. For example, the duration may be on the order of two minutes.

According to the presently disclosed techniques, a need to reduce pressure of the pressure vessel 404 below ambient pressure may be avoided. For example, it is contemplated that pressure in the pressure vessel 404 may be reduced from a maximal value of two atmospheres or greater to a minimum value of approximately ambient pressure (one atmosphere) or higher.

In some implementations, pressure in the pressure vessel 404 may be increased from one atmosphere to two or more atmospheres pressure at a rate substantially slower than the depressurization rate. In some implementations, the pressure may be held at the two or more atmospheres for a period of time sufficient to insure that interior portions of the test article 402 have reached pressure equilibrium with the chamber pressure.

Thus, improved techniques for testing a spacecraft component for compatibility with a depressurization profile associated with a launch vehicle ascent have been disclosed. It will be appreciated that the presently disclosed techniques avoid a need to rapidly evacuate the pressure vessel, which may be difficult or impossible to accomplish for a pressure vessel large enough to enclose large structural components such as spacecraft equipment and solar array panels. The disclosed techniques permit exposure of an entire as-built flight structural component to a depressurization environment that simulates, or permits demonstration of margin with respect to, a launch ascent depressurization profile. The disclosed test techniques may be implemented as part of an acceptance test program executed on flight hardware.

The foregoing merely illustrates principles of the invention. It will thus be appreciated that those skilled in the art will be able to devise numerous systems and methods which, although not explicitly shown or described herein, embody said principles of the invention and are thus within the spirit and scope of the invention as defined by the following claims.

What is claimed is:

1. A method comprising:
  testing a component for compatibility with a depressurization profile associated with a launch vehicle ascent, the testing including:
    raising a pressure within a pressure vessel containing the component to a first value not less than approximately two atmospheres absolute pressure;
    lowering the pressure within the pressure vessel at a rate simulating the depressurization profile; and
    inspecting the component for damage.

2. The method of claim 1, wherein the component is a panel comprising a honeycomb core sandwiched between two faceskins.

3. The method of claim 2, wherein a planar area of the panel is at least 25 square feet.

4. The method of claim 2, wherein a planar area of the panel is at least 100 square feet.

5. The method of claim 1, wherein the rate simulating the depressurization profile averages approximately 0.5 atmospheres per minute.

6. The method of claim 5, wherein lowering the pressure within the pressure vessel at the rate of approximately 0.5 atmospheres per minute is performed for a duration of greater than one minute.

7. The method of claim 5 wherein lowering the pressure within the pressure vessel at the rate of approximately 0.5 atmospheres per minute is performed by venting the pressure vessel to a pressure no less than ambient pressure.

8. The method of claim 1, wherein the rate simulating the depressurization profile has a maximal value of at least one atmosphere per minute.

9. The method of claim 1, wherein raising the pressure results in achieving substantially equal pressures in the pressure vessel exterior to the component and in interior portions of the component.

10. The method of claim 1, wherein the pressure vessel is an autoclave.

11. A method comprising:
  testing a component for compatibility with a depressurization profile associated with a launch vehicle ascent, the depressurization profile including a maximum expected ascent depressurization rate, the testing including:
    raising a pressure within a pressure vessel containing the component to a first value not less than approximately two atmospheres absolute pressure;
    lowering the pressure within the pressure vessel at a test depressurization rate that is greater than the maximum expected ascent depressurization rate; and
    inspecting the component for damage.

12. The method of claim 11, wherein the test depressurization rate is 1.5 times higher than the maximum expected ascent depressurization rate.

13. The method of claim 11, wherein the component is a panel comprising a honeycomb core sandwiched between two faceskins.

14. The method of claim 11, wherein the test depressurization rate averages at least 0.5 atmospheres per minute.

15. The method of claim 11, wherein lowering the pressure within the pressure vessel at the test depressurization rate is performed for a duration of greater than one minute.

16. The method of claim 11, wherein the test depressurization rate has a maximal value of at least one atmosphere per minute.

17. The method of claim 16, wherein lowering the pressure within the pressure vessel includes venting the pressure vessel to a pressure no less than ambient pressure.

18. The method of claim 11, wherein raising the pressure results in achieving substantially equal pressures in the pressure vessel exterior to the component and in interior portions of the component.

19. The method of claim 11, wherein the pressure vessel is an autoclave.

* * * * *